(12) United States Patent
Rak et al.

(10) Patent No.: US 10,102,043 B2
(45) Date of Patent: Oct. 16, 2018

(54) METHOD AND SYSTEM FOR MAPPING AN INTEGRAL INTO A THREAD OF A PARALLEL ARCHITECTURE

(71) Applicants: Furukawa Electric Technologiai Intezet Kft., Budapest (HU); Pazmany Peter Katolikus Egyetem, Budapest (HU); StreamNovation Kft., Budapest (HU)

(72) Inventors: Adam Rak, Karolyfalva (HU); Gergely Feldhoffer, Budapest (HU); Gergely Balazs Soos, Jaszbereny (HU); Tibor Holtzl, Budapest (HU); Balazs Oroszi, Vac (HU); Gyorgy Gabor Cserey, Budapest (HU)

(73) Assignees: Furukawa Electric Technologies Intezet Kft., Budapest (HU); Pazmany Peter Katolikus Egyetem, Budepest (HU); StreamNovation Kft., Budapest (HU)

( * ) Notice: Subject to any disclaimer, the term of this patent is extended or adjusted under 35 U.S.C. 154(b) by 604 days.

(21) Appl. No.: 14/404,854

(22) PCT Filed: May 31, 2013

(86) PCT No.: PCT/HU2013/000051
§ 371 (c)(1),
(2) Date: Dec. 1, 2014

(87) PCT Pub. No.: WO2013/179073
PCT Pub. Date: Dec. 5, 2013

(65) Prior Publication Data
US 2015/0128151 A1 May 7, 2015

(30) Foreign Application Priority Data
May 31, 2012 (HU) .................... 1200331

(51) Int. Cl.
*G06F 9/52* (2006.01)
*G06F 17/10* (2006.01)
*G06F 19/00* (2018.01)

(52) U.S. Cl.
CPC ............... *G06F 9/52* (2013.01); *G06F 17/10* (2013.01); *G06F 19/701* (2013.01)

(58) Field of Classification Search
None
See application file for complete search history.

(56) References Cited

U.S. PATENT DOCUMENTS

2015/0006316 A1* 1/2015 Zhou .................. G06Q 10/04
705/26.7

OTHER PUBLICATIONS

European Patent Office, Notification of Transmittal of the International Search Report and the Written Opinion of the International Searching Authority, or the Declaration, dated Jul. 7, 2014.
Koji Yasuda, "Two-electron integral evaluation on the graphics processor unit," Journal of Computational Chemistry, vol. 29 No. 3, 2007, pp. 334-342—Abstract Only.
David A. Bader et al, "Evaluating Arithmetic Expressions Using Tree Contraction: A Fast and Salable parallel Implementation for Symmetric Multiprocessors (SMPs)" In: "High Performance computing—HiPC 2002," Dec. 18, 2002, Springer Berlin Heidelberg, Berlin, Heidelberg.
Ramdas T et al, "ERI sorting for emerging processor architectures," Computer Physics Communications, Elsevier Science Publishers B.V., Amsterdam, NL, vol. 180, No. 8, Aug. 2009, pp. 1221-1229.—Abstract Only.
Ramdas T et al, "On ERI sorting for SIMD execution of large-scale Hartree-Fock SCF," Computer Physics Communications, Elsevier Science Publishers B.V., Amsterdam, NL, vol. 178, No. 11, Jun. 2008, pp. 817-834.—Abstract Only.
Stone J E et al, "GPU—Accelerated Molecular Modeling Coming of Age," Journal of Molecular Graphics and Modelling, Elsevier Science, New York, NY, vol. 29, No. 2, Sep. 2010, pp. 116-125.
European Patent Office, Notification of Transmittal of the International Preliminary Report on Patentability, dated Feb. 19, 2015.

* cited by examiner

*Primary Examiner* — Anna Skibinsky
(74) *Attorney, Agent, or Firm* — Wood Herron & Evans LLP

(57) ABSTRACT

A method is disclosed for mapping an integral into a thread of a parallel architecture, in the course of which the integral is mapped into a summation expressed by coefficient values and summation values, and a directed graph is generated corresponding to the computation of the summation. Furthermore, in the course of the method a level of a traversal sequence to each of the nodes is assigned, respectively, and at each level of the traversal sequence, a storage location of the intermediate value corresponding to the edge connected with its input to the node corresponding to the given level is specified in a memory corresponding to the thread and including a register storage, a local storage, and a global storage. A system is also disclosed for mapping an integral into a thread of a parallel architecture.

19 Claims, 5 Drawing Sheets

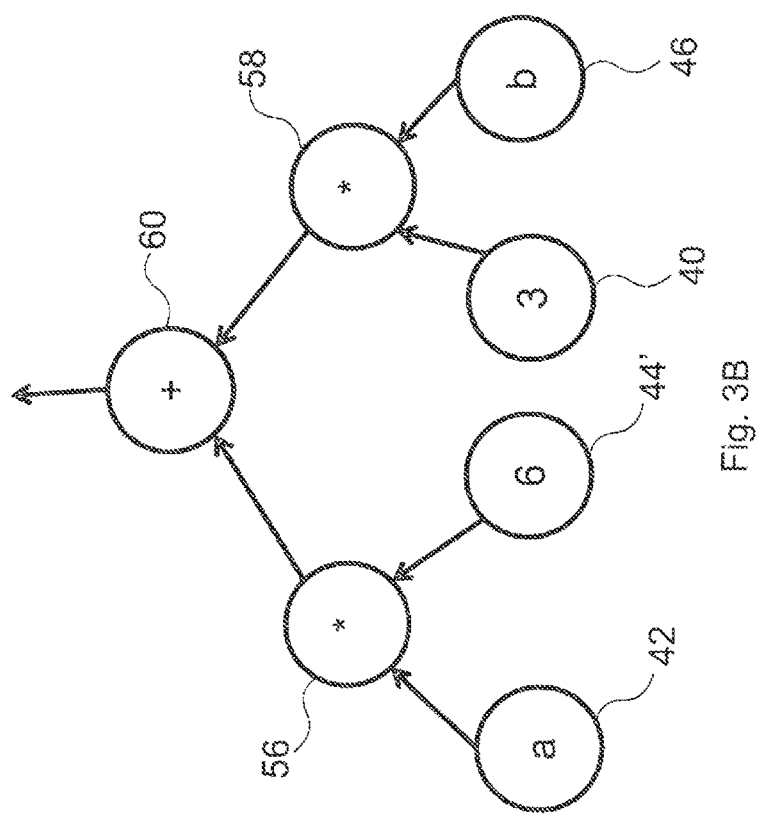
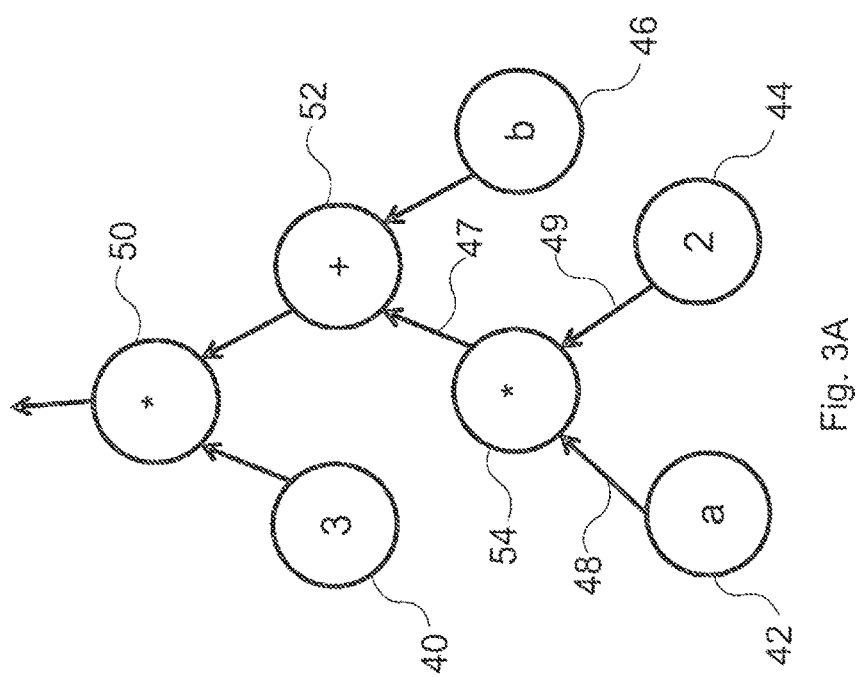
Fig. 3B
Fig. 3A

METHOD AND SYSTEM FOR MAPPING AN INTEGRAL INTO A THREAD OF A PARALLEL ARCHITECTURE

CROSS-REFERENCE TO RELATED APPLICATIONS

This application claims priority, under Section 371, to PCT Application No. PCT/HU2013/000051 filed on May 31, 2013, which in turns claims priority to HU P1200331, filed on May 31, 2012.

TECHNICAL FIELD

The invention relates to a method and system for mapping an integral into a thread of a parallel architecture.

DESCRIPTION OF PRIOR ART

Due to the advances in computer technology, quantum chemical simulators have improved significantly over the past decades. The recent improvements in computer technology, particularly in parallel architectures allow for the increasingly efficient computation of molecular integrals. For the purposes of atom and molecule simulations, molecular orbitals are taken to series expansion in atomic basis functions. The quantity and type of atomic basis functions corresponding to an atom to be simulated are decisive for the accuracy of calculations required for atom and molecule simulations. Simple basis functions are characterised by angular momentum (the angular momentum corresponding to s, p, d, f, g, h, . . . orbitals), and exponent, while complex (so-called contracted) basis functions are characterised by their linear coefficients (the so-called contraction coefficients).

The speed of quantum chemical computations is basically determined by the speed of the integration, and first of all the speed of computing the two-electron integrals, since in case of n basis functions, $n^4$ two-electron integrals have to be computed. This latter number is in the order of millions even for a simple molecule. Since two-electron integrals may be computed independently of one another, quantum chemical computations are parallelizable their nature.

The accuracy of quantum chemical calculations is affected by the number and quality of basis functions taken into account for computing two-electron integrals. In essence, the "quality" of basis functions is determined by the highest angular momentum for which the corresponding basis functions are still taken into account for the computations. Basis functions having higher angular momentum than this given angular momentum value are discarded; however, in case basis functions are taken into account up to a sufficiently high angular momentum for the size of the molecule (compared to essentially to the number of charged particles of the molecule), an acceptable accuracy can be achieved. Usually, i.e. even in case of simple organic molecules, at least f-type functions have to be taken into account for calculations with acceptable accuracy, however, for more accurate computations of larger molecules, g and h-type basis functions also have to be taken into account. A problem is posed by the fact that the integrals (usually two-electron integrals) occurring in quantum chemical calculations become more and more complex in structure as the angular momentum of the basis functions increases, and therefore their computation has increasing computing cost or demand.

Due to their adaptability to parallel processing, quantum chemical computations have several known implementations on GPU (Graphics Processing Unit). However, these GPU implementations are either not capable of integrating basis functions above type d, or are capable of such operations only with extremely high computing cost. The reason for this is that in the most conventional implementations recursion is applied for computing the integrals, and solutions based on recursion are not optimal on GPU due to the highly excessive memory demand and the high number of memory operations.

Another possible solution—which, however, is not a widespread application—is expanding the numeric formula corresponding to the integral. In this case, millions of multiplications and additions have to be performed for computing a single integral. The GPU-optimization of this operation is, as far as register assignment is concerned, a so-called NP-hard problem (Non-deterministic polynomial type, see for instance http://en.wikipedia.org/wiki/NP-hard). A further problem associated with the expansion of the numeric formula is that the source code of the simulation is overly large (it may often have a million lines), and a code of such size cannot be compiled for GPU utilizing conventional compilers.

Known methods for computing molecular integrals are disclosed in a paper by P. M. W. Gill (P. M. W. Gill: Molecular integrals over Gaussian basis functions, Advances in Quantum Chemistry Vol. 25, pp 141-205 (1994); in the following: Gill's review).

In light of existing solutions a need has arisen for providing a method that is capable of mapping molecular integrals, particularly a multitude of parallelly computable two-electron integrals, and other more complex integrals (i.e. integrals requiring numerical solution) into a parallel architecture requiring lower computation demand than do existing solutions.

DISCLOSURE OF THE INVENTION

The primary object of the invention is to provide a method and system that reduces or eliminates the drawbacks of prior art solutions to the greatest possible extent.

A further object of the invention is to provide a method and system that is capable of mapping the computation of integrals into a respective thread of a parallel architecture such that the integrals may be computed in a manner that is more optimal and has lower computation demand and cost than known solutions.

Because of the high computation demand, in the method according to the invention, the choice of computing platform has been driven by the efficiency of the architecture. As the GPU is one of the architectures that are most dynamically increasing in computing power, the method according to the invention is e.g. optimized for the memory architecture applied also in GPU-s (register storage, local storage, global storage).

The method according to the invention involves mapping an integral into a thread of a parallel architecture, preferably a GPU, by expanding a summation obtained for the given integral. To increase the efficiency of the method according to the invention, the memory architecture of the parallel architecture (GPU) is heavily exploited. The method and system according to the invention is capable of mapping not only molecular integrals, but also other integrals that can be converted into summation, into a thread of a parallel architecture. The method and system according to the invention relates to the mapping of a molecular integral, the computation of the integral is not comprised in the method according to the invention.

The objectives according to the present invention have been fulfilled by providing the method described below, and the system described below. Preferred embodiments of the invention are defined below.

BRIEF DESCRIPTION OF THE DRAWINGS

Preferred embodiments of the invention will be explained below referring to the accompanying drawings, where FIG. 3A shows a partial view of a directed graph exemplary applied in the method according to the invention, FIG. 3B illustrates an equivalent of the graph part shown in FIG. 3B.

MODES FOR CARRYING OUT THE INVENTION

Figure 1:
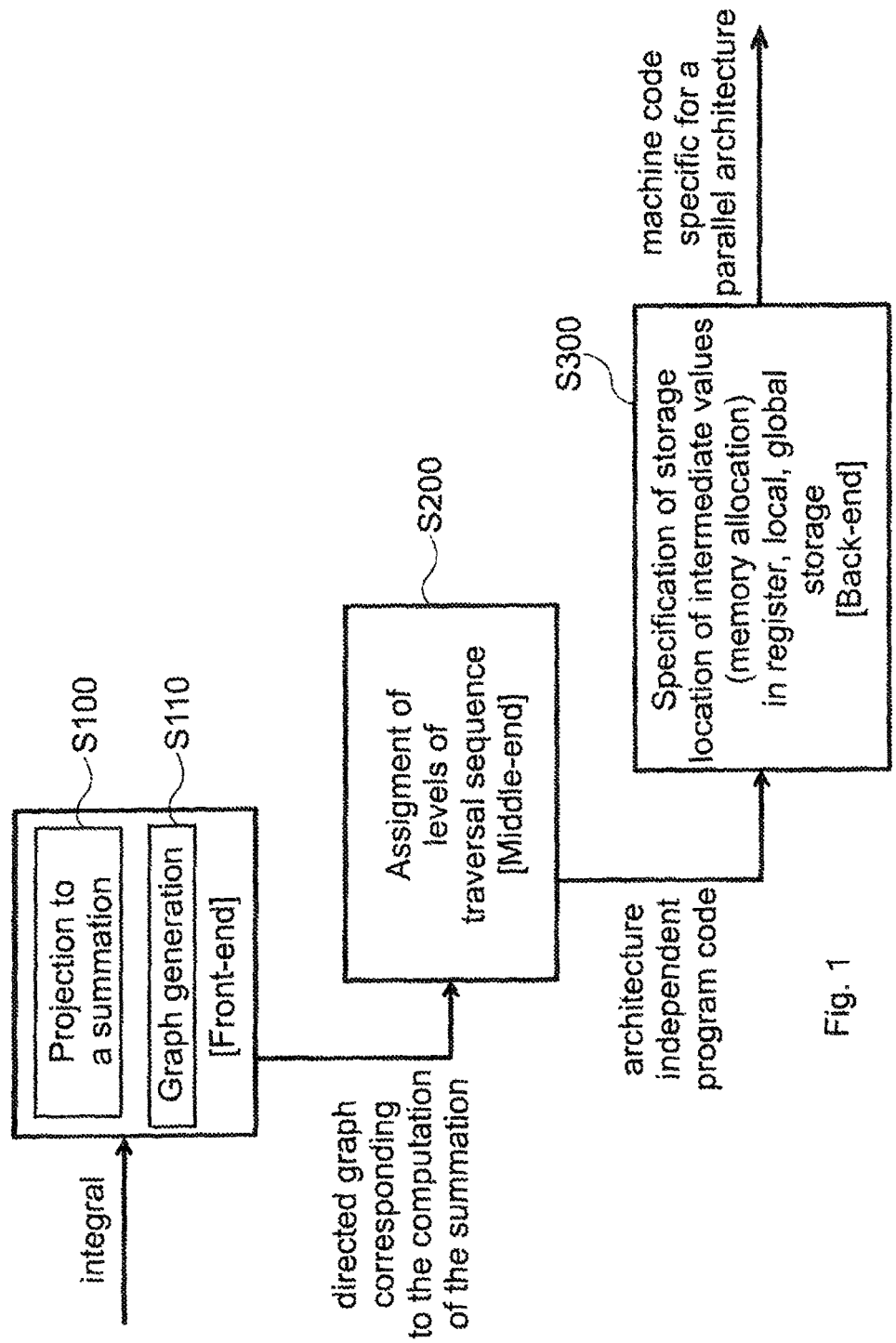
FIG. 1 shows a flow chart illustrating an embodiment of the method according to the invention.

FIG. 1 shows a flow chart illustrating the inventive method adapted for mapping an integral into a thread of a parallel architecture. FIG. 1 illustrates that at the beginning of method, in operational step S100, the integral is mapped into a summation expressed utilizing coefficient values and summation values. In a number of cases, components of the summation can be computed applying easily computable integrals.

In a general case, the summation obtained in case of molecular integrals is very complex, even for small molecules, it comprises a great number of summation indices on which the coefficient values and the corresponding summation values—to be multiplied with the coefficient values—depend. Thereby, the method according to the invention is capable of transforming many different types of integral into summation, and thus of mapping integrals into a thread of a parallel architecture. However, the process of transforming the integral into summation will now be explained for a two-electron exchange integral. Gill's review paper that has already been referred to above considers certain relevant integral types.

The two-electron exchange integral is defined by the following formula:

$$(ab \mid cd) := \int\int\int_{r_1}\int\int\int_{r_2} \Phi_a(r_1)\Phi_b(r_1)\frac{1}{r_{12}}\Phi_c(r_2)\Phi_d(r_2) dr_1 dr_2$$

The exchange integral is a common type for calculations in atom or molecule simulations. The exchange integral describes the exchange interaction among electrons of a given atom or molecule. The integrand of the integral in question contains basis functions of quantum mechanical wave functions which are expanded in some basis during the transformation into summation. Below is presented a possibly applicable basis; the integral may also be expanded utilizing other bases. In the formula, $r_{12}=r_1-r_2$. Basis functions $\phi_i$ may be expanded as follows:

$$g(r, R, \alpha) := e^{-\alpha|r-R|^2}$$

$$\mathcal{A}_{poly}(r, R, a) := (r_x - R_x)^{a_x}(r_y - R_y)^{a_y}(r_z - R_z)^{a_z}$$

$$\Phi(r) := \mathcal{A}_{poly}(r, R, a) \sum_i c_i g(r, R, \alpha_i)$$

The functions g are Gaussian functions, and $A_{poly}$ is the angular polynomial applied for the expansion. R is the location vector of the center of the basis function $\phi(r)$ (cf. Gill's review). Constants $\alpha$ and $c_i$ are the so-called contraction coefficients.

Substituting the basis functions as expanded in an elementary basis into the two-electron exchange integral $(ab|cd)$ the following expansion is obtained multiplying linear combinations out of the integral:

$$(ab \mid cd) = $$
$$\sum_i \sum_j \sum_k \sum_l ca_i cb_j cc_k cd_l \int\int\int_{r_1}\int\int\int_{r_2} \mathcal{A}_{poly}(r_1, A, a)$$
$$g(r_1, A, \alpha_i)\mathcal{A}_{poly}(r_1, B, b)g(r_1, B, \beta_j)\frac{1}{r_{12}}\mathcal{A}_{poly}(r_2, C, c)$$
$$g(r_2, C, \gamma_k)\mathcal{A}_{poly}(r_2, D, d)g(r_2, D, \delta_l)dr_1 dr_2$$

In the formula, the location vectors of the centers of basis functions $\phi_a$, $\phi_b$, and $\phi_d$, respectively, are denoted by A, B, C, and D. The constant coefficients of the linear combinations are denoted by $ca_i$, $cb_j$, $cc_k$ and $cd_l$. The equation cannot be computed utilizing any direct method, except when the integral has a simple, i.e. (ss|ss) form.

Since the product of Gaussian functions yields a Gaussian function, the side ab may be combined into p, and the side cd into q:

$$g(r_1, A, \alpha_i)g(r_1, B, \beta_j) \Rightarrow g(r_1, P, \zeta_{ij})$$
$$g(r_2, C, \gamma_k)g(r_2, D, \delta_l) \Rightarrow g(r_2, Q, \zeta_{kl})$$

This combination is simple only considering the parameters, but is complex on the level of the rules of deduction (cf. Gill's review).

The two-electron integral $(ab|cd)$ may be written as a summation:

$$(ab \mid cd) = $$
$$\sum (\mathcal{P}_{prefactor}(A, B, C, D, \alpha, \beta, \gamma, \delta) \cdot \mathcal{F}(A, B, C, D, \alpha, \beta, \gamma, \delta, m)),$$

where the expression $$\left(\int\int\int_{r_1}\int\int\int_{r_2} g(r, A, \alpha)g(r, B, \beta)\frac{1}{r_{12}}g(r, C, \gamma)g(r, D, \delta)dr_1 dr_2\right)^{(m)} \approx$$
$$\mathcal{F}(A, B, C, D, \alpha, \beta, \gamma, \delta, m)$$

defines a function F (the summation value according to the invention) dependent on several different values, and where (m) is used to denote the m-th order derivative with respect to the variable t (to be introduced below, cf. Gill's review). $P_{prefactor}$ (the coefficient value according to the invention) can be given by the following expression:

$$\mathcal{P}_{prefactor}(A, B, C, D, \alpha, \beta, \gamma, \delta) := (B-A)^{a^*} \cdot (C-D)^{b^*} \cdot (D-B)^{c^*} \cdot$$
$$(C-A)^{e^*} \cdot (D-A)^{f^*} \cdot (C-B)^{g^*} \cdot (R)^{r^*} \cdot \frac{(2\alpha)^{a'}(2\beta)^{b'}}{(2\zeta)^{p'}} \cdot \frac{(2\gamma)^{c'}(2\delta)^{d'}}{(2\eta)^{q'}},$$

where the exponents a*–r*; and a'–q' are obtained during the integral expansion algorithm, and where $\zeta = \alpha + \beta$ and $\eta = \gamma + \delta$.

In essence, a quartet—that is, a two-electron integral—is deducted for the sum of the functions F( . . . , m) (in the following: $F_m$ functions) multiplied symbolically by the coefficients $P_{prefactor}$. It has to be borne in mind that—for large enough molecules—this sum may even comprise many millions of terms. The object of integral computation algorithms, capable for instance of computing exchange integrals, is to provide as efficient a way for computing the integral as possible. For instance, known methods apply multiplying out in performing the summation, thereby avoiding to compute all of the terms of the summation. Essentially, in the course of the method according to the invention, the summation is partially expanded by applying multiplying out.

As it is seen from the formula, $P_{prefactor}$ depends on all summation indices, i.e. there are potentially as many $P_{prefactor}$ values as there are elements in the summation; in addition to these, the function $F_m$ has only one variable parameter m. As it is apparent from the definition of the function F, the parameter m is the order of the derivation. According to the rules of the integral expansion, m can have as many possible values as the sum of angular moments in the given two-electron integral. Thus for instance, in case of a (pp|pp) type two-electron integral, m may have four different values, m=0 . . . 4.

Based on mathematical considerations, all the parameters of the function $F_m$ different from m ($\alpha$, $\beta$, $\gamma$, $\delta$) can be combined in a single parameter t mentioned above, because of the rotational symmetry of the Gaussian functions. Thereby, it is the function $F_m(t)$ that has to be computed:

$$\mathcal{F}_m(t) := \sqrt{\frac{2}{\pi}} \int_0^1 x^{2m} e^{-t \cdot x^2} dx$$

Below is presented the Chebyshev-approximation of the functions $F_m(t)$. The Chebyshev polynomials can be defined by the following recursive formula:

$T_0(.r)=1$ $T_1(.r)=.r$ $T_{n+1}(.r)=2.rT_n(.r)-T_{n-1}(.r).$

According to the formula, the second-order Chebyshev polynomial would be $T_2(x)=2x^2-1$. According to the formula $$f(x) \sim \sum_{i=0}^{\infty} c_i T_i(x)$$

all at least twice differentiable functions can be approximated by Chebyshev polynomials in a suitable norm. To approximate the functions $F_m$, a Chebyshev-approximation shown in the above formula is applied, with the provision that the terms included in the summation of the approximation of the function are taken into account only up to the maximum accuracy provided by the currently applied number representation (for instance, 32-bit or 64-bit floating point representation). Since they do not affect accuracy, all the other terms are discarded.

Although $F_m$ may be computed in several different ways, methods applying pre-stored tables are not optimal for parallel architectures, because they would result in suboptimal memory access patterns. Iterative methods are much more suited for application on parallel architectures, such as GPU-s. There are two different known methods for the iterative computation of $F_m$: a so-called forward iteration, and a so-called back-and-forth iteration method.

Forward iteration is extremely efficient, because in each step an $F_m$ is computed for a given m, however, for the t<20 values of the above introduced combined parameter t, the iteration exponentially diverges away from the correct solution.

Forward iteration may be defined by the following formula:

$$\mathcal{F}_0(t) = \sqrt{\frac{2}{\pi}} \frac{\text{Erf}(\sqrt{t})}{\sqrt{t}}$$

$$\mathcal{F}_{m+1}(t) = \frac{(2m+1)\mathcal{F}_m(t) - e^{-t}}{2t}$$

where Erf(t) is the Gaussian error function.

Back-and-forth iteration, on the contrary, diverges in case t>20, and thereby the two iterative methods complement each other well; however, back-and-forth iteration is not GPU-optimal. Therefore, a Chebyshev-approximation is preferably applied as described below.

In an embodiment of the invention, the functions $F_m$ are computed as follows. The instability of forward iteration for t<20 is ignored, but when the iteration starts to be inaccurate, we switch to Chebyshev-approximation. This is performed by providing in the generated code a corresponding iteration step based on Chebyshev-approximation for iteration steps belonging to each m. It is then decided based on the value of t in runtime whether the approximation is stable in the given step, and in case of instability the Chebyshev-approximation is applied. The Chebyshev-approximation is not applied exclusively because, for numerical reasons, the accuracy of forward iteration exceeds the accuracy of Chebyshev-approximation, provided that the iteration is stable.

The iteration aided by Chebyshev-approximation is therefore performed as follows:

$$\mathcal{F}_0(t) = \sqrt{\frac{2}{\pi}} \frac{\text{Erf}(\sqrt{t})}{\sqrt{t}}$$

$$\mathcal{F}_{m+1}(t) = \begin{cases} \frac{(2m+1)\mathcal{F}_m(t) - e^{-t}}{2t} & \text{if } (m, t) \text{ is stable} \\ \mathcal{F}_m(t) \sum_{i=0}^{\infty} c_{m,i} T_i(t) & \text{if } (m, t) \text{ is unstable} \end{cases}$$

In accordance with what has been presented above, in a preferred embodiment of the invention a hierarchical order of the summation values of the summation, i.e. the series of $F_m$ functions, is obtained by iteration, where the lowest order of summation values is initialized numerically and the computational stability of the higher orders of the hierarchical order of the summation values is investigated, and, based on the lowest order, the higher orders are computed applying forward iteration in case of computational stability, or applying iteration based on Chebyshev-approximation in case of computational instability.

The coefficients $c_{m,i}$ of the Chebyshev polynomials—being different on each iteration level—are numerically determined in compilation time utilizing a standard Chebyshev approximation algorithm. The values of the parameters m and t for which forward iteration will be unstable may be determined applying numerical simulation, and the results can be built in the code. To provide optimum implementation for GPU, the iteration thus obtained is applied not as a loop but in unrolled state, such that program code is compiled for each iteration step. Using the above formula, the Chebyshev polynomials are fitted on the ratio $F_{m+1}(t)/F_m(t)$ (as it is apparent from the equations), providing, according to our measurements, the highest-accuracy results.

In the course of the method according to the invention, after the determination of the summation, in operational step S110 of FIG. 1 a directed graph is generated corresponding to the computation of the summation. To represent the expansion thereof, a computational data stream can be made to correspond to the summation. With the help of graph theory, the computational data stream can be mathematically represented by a so-called directed tree having nodes and directed edges. FIGS. 3A and 3B show a part of a graph exemplifying the type of graph applied in the method according to the invention. The graph part shown in FIG. 3A is included to illustrate the types of graph applicable for the purposes of the method according to the invention, the actual structure of the graph, as well as the values and operations located at the nodes are shown by way of example only.

The graph applied in the method according to the invention is described referring to FIG. 3A. The directed graph applied in the method according to the invention comprises input nodes corresponding on the one hand to the coefficient values of the summation and on the other hand to the summation values, the input nodes being connected to the input of a respective edge 48, 49, and being adapted for giving their values, as intermediate values, to the edges connected thereto with their inputs. FIG. 3A shows input nodes 40, 42, 44, 46. Each input node has a value that is given to the single edge connected to the node, this edge is always connected to the input node with its input. Since each one of the coefficient values and the summation values of a summation has a corresponding input node, input nodes constitute the lowest and widest layer of the directed graph applied in the method according to the invention.

The directed graph applied in the method according to the invention further comprises at least one intermediate node each corresponding to one operation of the summation, and being connected to outputs of two edges—for instance, edges 48, 49—and to an input of one edge—for instance, edge 47—, and being adapted for performing the operation on the values of the edges connected thereto with their outputs, and for giving the result of the operation to the edge connected thereto with its input as an intermediate value. Intermediate nodes 50, 52, 54 are also shown in FIG. 3A. Contrary to the input nodes, one operation corresponds to each intermediate node, which operation is performed on the values supplied by the incoming edges, the result being fed to the edge connected with its input to the given intermediate node. As it is illustrated in the drawing, the outgoing edge corresponding to the result may then provide the input value for a subsequent intermediate node.

The result of the summation may be a single number, in this case the directed graph corresponding to the summation has a single ultimate target node. In some cases more than one integrals are computed through a single summation, and thereby, by a thread, which e.g. belong to the same shell and differ only in the configuration of angular momentum. In these cases the results are obtained for all the integrals in question. In case the end result is a single number, the graph comprises a single output node connected to, and receiving the intermediate value of, the output of the edge corresponding to the intermediate value belonging to the complete summation (that is, the edge that contains the output of the last operation of the graph). If there are multiple output values, then the directed graph may comprise more than one output nodes that are connected to the output of the edge corresponding to an intermediate value belonging to at least a part of the summation, the output nodes receiving its intermediate value. FIG. 3A does not show any output node.

In a next operational step S200 of the method according to the invention a level of the traversal sequence is assigned to each of the nodes, respectively. In this step the sequence is specified in which the nodes are executed in a thread of the parallel architecture. Executing an input node means that the input nodes give their values to the outgoing edge connected to them with its input. The traversal sequence has to be specified because one thread is capable of performing only one operation at a time. Apart from setting the input values (that is, in essence, the initialization of the task) a single operation is performed at each level of the traversal sequence. By specifying the traversal sequence, the graph is essentially "serialized".

Figure 2:
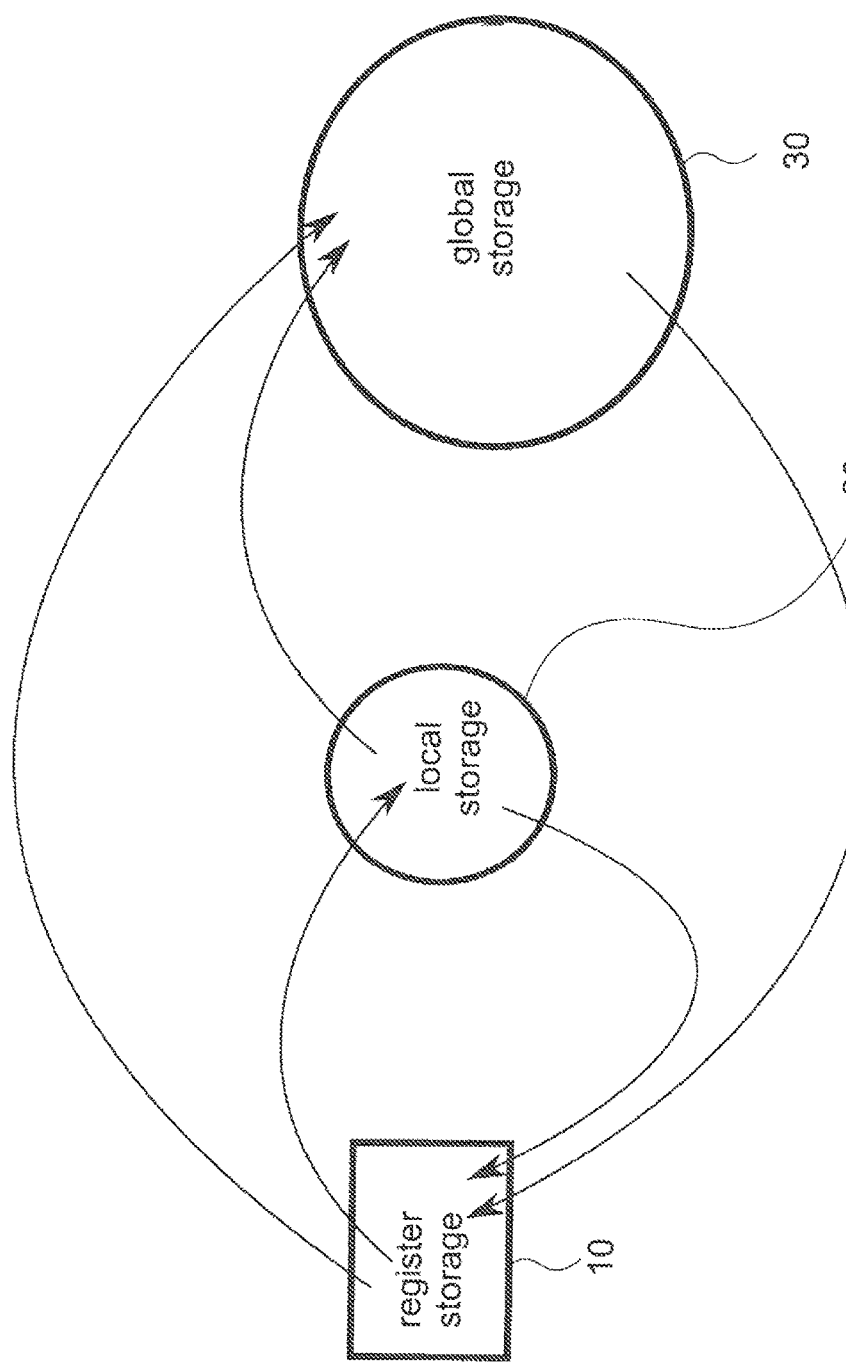
FIG. 2 illustrates the memory structure and the direction of memory operations between storage locations of different storage types applied for the method according to the invention.

The traversal sequence also determines when the values corresponding to the outputs of the individual nodes will be needed again, until then these values are stored. Thereby, in a next operational step S300 of the method according to the invention (shown in FIG. 1), at each level of the traversal sequence a storage location of the intermediate value corresponding to the edge connected with its input to the node corresponding to the given level is specified in a memory corresponding to the thread. The memory comprises a register storage 10, a local storage 20, and a global storage 30. Storages 10, 20, 30 are illustrated in FIG. 2. Possible transfer paths between storages 10, 20, 30 are shown by arrows in FIG. 2. A given value always leaves a thread through the register storage 10, its storage location to be assigned either in the register storage 10 itself or further down in the local storage 20 or global storage 30. As shown by the arrows at the bottom of FIG. 2, data may be fetched into the register storage 10 from the local storage 20 and also from the global storage 30.

In the parallel architectures applied according to the invention, such as in a GPU, three types of memory storage are utilized. The first storage type, which has the fastest access time, is the register storage. The GPU is capable of performing operations only via registers. Though the exact number of registers is dependent on GPU type, register storage is the most limited storage type in GPU-s. For instance, the NVIDIA Fermi GPU has 63 pieces of 32-bit registers assigned to each thread.

The second type of memory, somewhat slower than register storage but still reasonably fast, is local storage or memory that is arranged on the GPU chip beside the cores processing the computational threads. The size of the local storage is generally 48 KB, which is shared usually by 512 or 256 threads. In case of the NVIDIA Fermi GPU, a local storage unit is shared by 256 threads, allowing the storage of 48 float values (32-bit single-precision floating point values) for each thread.

The third type of storage is the global memory, which is installed in the form of DRAM chips on the GPU card. Global storage is the slowest, and has the largest size, of the storage types, and it also has significant access time. The size of global storage installed on modern GPU-s is at least 1 GB, the maximum amount usually being 6 GB. In the method according to the invention a parallel architecture having 2 GB of global memory is preferably applied.

In a preferred embodiment of the method according to the invention, after the directed graph has been specified, at least one equivalent transformation is performed on the directed graph. The equivalent transformation that can be performed in this operational step is illustrated in FIGS. 3A and 3B. In a general case, an equivalent transformation of the type illustrated in the drawings is a lot more complex task than the transformation performed in the example shown, but such transformations may be applied for changing the local depth and the width of the graph.

Graph parts shown in FIGS. 3A, 38 are equivalent in the sense that both graph parts submit the same value to their respective outputs, i.e. their topmost outgoing edges. Therefore, such equivalent transformations are preferably performed on the graph processed during the method according to the invention in order to decrease the number of the levels of the directed graph such that the number of operations (i.e. intermediate nodes) do not increase. Similarly to FIG. 3A, FIG. 3B shows a part containing 3 intermediate nodes; they are intermediate nodes 56, 58, 60.

In addition to the illustrated equivalent transformation, sign optimization may also be performed, consisting e.g. the combination of the signs of certain multiplications with that of the constants.

In a further preferred embodiment of the method according to the invention, after the traversal sequence has been established, the level at which the given intermediate value is utilized as the input of the operation corresponding to an intermediate node is specified for each intermediate value, and the value of the intermediate level parameter belonging to the given intermediate level is set to the number of levels remaining before the given level. According to this step, an intermediate level parameter is assigned to every intermediate value. The intermediate level parameter is a number specifying how many temporal levels elapse from the time the corresponding intermediate value is computed until the given intermediate value is utilized.

In the present embodiment, as the traversal is being performed according to the traversal sequence, the storage location of the intermediate value corresponding to the levels of the traversal sequence is assigned in the register storage 10, in the locale storage 20, or in the global storage 30 as presented below.

A storage location for the given intermediate value is assigned in the register storage 10,
if the register storage 10 has free storage space, or
if there is such an intermediate value that has its storage location assigned in the register storage 10 and has an intermediate level parameter that is larger than the intermediate level parameter of the given intermediate value, and the storage location of the intermediate value having the highest intermediate level parameter value of those assigned to the register storage 10 is changed to a storage location in the local storage 20 or in the global storage 30 based on the value of the intermediate level parameter.

The latter condition is of course evaluated only in case there is no free storage space in the register storage 10, or in other words, all storage locations thereof have been assigned. In case the latter condition is fulfilled and the storage location of the given intermediate value is assigned in the register storage 10, the register storage 10 would have one storage location more assigned than there is space in it. Thereby, if the second condition is fulfilled, it also has to be provided that a storage location is reassigned (moved) to the storage coming next in the memory hierarchy, that is, the local storage 20, or the global storage 30.

If neither of the conditions for assigning a storage location in the register storage 10 has been fulfilled, then, according to the conditions, the register storage 10 is full (all of its storage locations have been assigned to an intermediate value), and thus an attempt is made for assigning a storage location for the given intermediate value in the local storage 20 that comes next in the hierarchy. A storage location for the given intermediate value is assigned in the local storage 20,
if the local storage 20 has free storage space, or
if there is such an intermediate value that has its storage location assigned in the local storage 20 and has an intermediate level parameter that is larger than the intermediate level parameter of the given intermediate value, and the storage location of the intermediate value having the highest intermediate level parameter value of those assigned to the local storage 20 is changed to a storage location in the global storage 30.

The conditions for assigning a storage location in the local storage 20 are similar to those of assigning a location in the register storage 10. If the local storage 20 is also full before the storage location of the given value is assigned, but, based on the values of the intermediate level parameters the storage location of the given intermediate value is still assigned in the local storage 20, then, in a manner similar to the above, a storage location assignment has to be moved from the local storage to the global storage 30.

In case the conditions of assigning a location in the register storage 10 or the local storage 20 are not fulfilled, then the storage location of the given intermediate value is assigned in the global storage 30. Accordingly, a storage location is assigned in the global storage 30 in case there is no free space either in the register storage 10 or in the local storage 20 (because if there were, the storage location for the given intermediate value would have been assigned there). In addition, the storage location for a given intermediate value is assigned in the global storage 30 only in case the values of the intermediate level parameters of all intermediate values stored in the register storage 10 and in the local storage 20 are smaller than the intermediate level parameter of the given intermediate value.

In an embodiment of the invention the above described assignment is performed such that, prior to assigning storage locations to the intermediate values belonging to the individual levels, two locations are assigned in the register storage 10 for values of edges connected with their outputs to the node corresponding to the operation assigned to the given level of the traversal sequence, that is, at each level, for the inputs of the operation. By assigning these two locations it is provided that no complex data relocations are necessary prior to executing the operation corresponding to the given level of the traversal sequence for ensuring that the intermediate values required for executing the operations are in the register storage 10. Also, assigning the storage location of the intermediate values in the above manner allows that the intermediate values to be utilized for the operation corresponding to the given level can be accessed as quickly as possible, since the inputs of the operation will be stored near one another, preferably in the register storage 10, or the local storage 20.

By assigning a storage location for individual intermediate values in the above described manner, in essence a so-called heuristics is applied. The most important consideration of the heuristics detailed above is the time when the given intermediate values are to be used again, that is, the time when the operation for which they serve as inputs is to be executed.

Advantages of the application of the heuristics compared to known algorithms will now be presented. In a first approximation, the execution of the heuristics applied in a preferred embodiment of the method according to the invention has a speed of O(n) (on the order of n), where n is the number of operations, i.e. essentially the number of the nodes. The speed O(n) corresponds to the fact that, in the embodiment detailed above, all instructions, that is, all the operations of the serialized graph, should be run across once, that is, a single traversal of the graph should be performed according to the traversal sequence. Only a constant number of steps are performed at each level of the traversal sequence (the intermediate level parameter of the intermediate elements assigned in the local storage and the register storage is examined). Since the speed of the examination of the intermediate level parameters can be estimated by O(log(n)), the execution of the complete heuristics—that is, the execution of memory allocation—can be estimated over by O(n·log(n)), so the time and storage complexity thereof is O(n·log(n)).

Therefore, the speed of memory allocation allows the above heuristics to process extremely large summations, even summations consisting of several billion elements, in a manageable time, that is, the computer program implementing the method according to the invention become compilable in case of a complexity of O(n·log(n)). In case of conventional compilers applied for programs having millions of instructions, time and storage complexities of O(n$^2$), or even O(n$^3$) may occur, which would be unacceptable for a summation equivalent to the integral to be computed. If the complexity of memory allocation, and thus the entire program code, exceeds O(n·log(n)), then the memory usage of the compiler for a source code of such size (consisting of so many instructions) may become so high that the compiler will be unable to finish (will exit with an error) due to excessive memory usage.

In an embodiment of the method according to the invention, instead of tracking the intermediate values themselves during assigning the storage locations, i.e. during memory allocation, so-called hashes, called "denoting values" in the context of the present document, are assigned to the intermediate values.

Since in the embodiment of the method according to the invention that applies denoting values the principle of the so-called denoting value tables is made use of, it is briefly summarized below. The task is to store data elements in a table, and then to access certain data elements present in the table. If the data elements themselves are applied for identifying the data elements in the table, the entire table should be examined to find out whether a given element is present in the table. Since the most important action to be performed on such a table is to search data elements, going through the entire table during each search is unacceptably slow.

The application of the so-called hash table, i.e. denoting value table gives a solution to this problem. In a first step, memory is allocated for the entire table, that is, a memory portion is assigned where all entries of the table can be stored. Memory locations of the allocated space may be addressed utilizing data element indices. Therefore, a function is defined of which the domain is the set of data elements and the codomain is the memory address range allocated for the table, i.e. the data element indices. It is important that this function should have a uniform distribution on the domain of data element indices, i.e. on the memory addresses. It can thereby provided that the function is capable of designating all the addresses of the allocated memory part. The function specifying the mapping between the data elements and their addresses is the hash function. Because a pseudo-random number generator is capable of generating uniformly distributed numbers from any input, a hash function can be realized utilizing a pseudo-random number generator. The distribution of the output of a pseudo-random number generator is guaranteed to be uniform and is statistically well-behaved, and at the same time is completely deterministic for the input, and thus it provides a good hash function.

The hash function is thereby applied for assigning for each data element an index in the table, which index is in effect the hash, or in other words, the denoting value itself. Thereby, the hash function can be utilized to establish the location of a data element in the table in a manner for which only the data element itself is required, without running a search on the complete table. It is theoretically possible that the hash function assigns the same index for two different data elements, but such a case occurs very rarely. This phenomenon may be handled utilizing known algorithms that provide that a single index in the table, that is, a single denoting value, does not have more than one corresponding data element.

By applying denoting values for the purposes of the method according to the invention, two intermediate values can be compared in compilation time, i.e. during the mapping operation, without computing the given intermediate values. In other words, we would like to know whether two given intermediate values occurring at two different locations in the traversal sequence are equal independent of the input values of the integral. This information is very important, because it allows efficient optimization. On a theoretical level there is another solution for testing the equivalence of two intermediate values obtained through different computational paths. This involves performing equivalency analysis on the computational trees, that is, the operations through which the given intermediate values were computed. Determining equivalence in such a manner is an NP-hard problem, which would pose a serious issue because a large number of such comparisons have to be made: when performing optimization of the graph corresponding to the summation it is an important consideration that, if possible, a given intermediate value should not be computed twice, but, instead, the earlier computed intermediate value should be used for its equivalent intermediate value.

In an embodiment of the method according to the invention a hash function is defined for the intermediate values in a manner described above. Because of the deterministic nature of the hash function it is guaranteed that if two intermediate values are equal then their denoting values obtained by the hash function will also be equal. Usually, this statement will also hold true in the reverse direction; it is very rare that two denoting values are equal erroneously, since a 64-bit number is preferably used as a denoting value, that highly reduces the chance of a random collision. A denoting value can thus assume one of $2^{64}$ possible values, among which the generated denoting values are distributed substantially uniformly.

Figure 4:
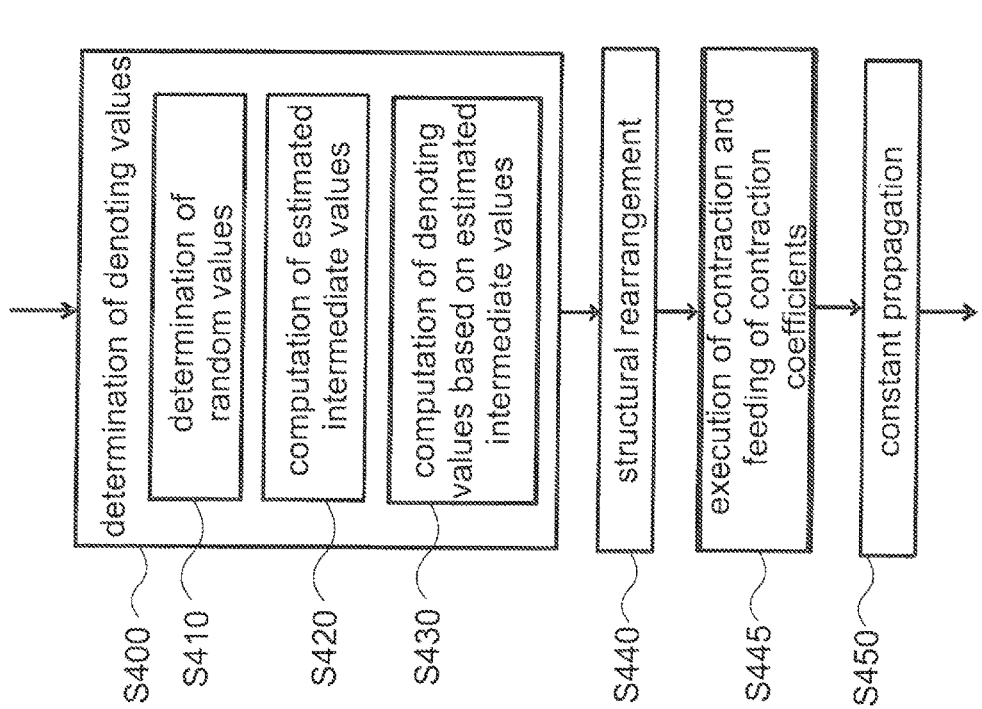
FIG. 4 shows a part of an embodiment of the method according to the invention.

In this embodiment of the method according to the invention, an operational step S400 for determining the denoting values is illustrated in FIG. 4. The application of denoting values also makes it simpler to compute the intermediate level values. In the present embodiment, intermediate level values can be determined performing the following steps. First, in operational step S410, at least one respective random value is sequentially fed to the input nodes. Subsequently, in operational step S420, at least one respective estimated intermediate value is sequentially obtained at edges connected with their inputs to the intermediate nodes, and, in operational step S430, a respective denoting value is assigned to each edge based on the at least one estimated intermediate value, and the intermediate level parameters being assigned to the intermediate values based on a denoting value table comprising the denoting values and the levels corresponding thereto. In these steps the denoting values are assigned to the estimated intermediate values, but, as it will be shown below, by the selection of the random values given as inputs it can be provided that these denoting values could correspond to real values of intermediate values.

In an embodiment of the method according to the invention multiple, preferably 20-110, particularly 30-40 respective random values are sequentially fed to the input nodes. In a further embodiment of the method according to the invention the multiple random values are selected in a uniform manner from a characteristic range of input values.

Based on the above, the hash function may be produced by executing the operations of the intermediate nodes 30 times, each time with random inputs that are preferably chosen such that they substantially cover the range of possible input values. An estimation is thereby obtained for each intermediate value. In an embodiment of the method according to the invention the denoting values are subsequently generated, based on the estimated intermediate values, as follows. First, shuffled values are generated by shuffling the bits of the estimated intermediate values deterministically, according to a predetermined sequence of operations, and the denoting values are determined by sequentially applying XOR logical operations to the shuffled values and separately combining each result with a respective shuffled value for each estimate of an intermediate value. Thereby, applying bit shuffling and the XOR logical operation a single denoting value (preferably a 64-bit number) is obtained on the basis of several estimated intermediate values. As seen from the above discussion, the above detailed requirements are fulfilled by the denoting value: if two intermediate values are equivalent, then the same denoting value is generated for them, and since the denoting values have been generated by bit shuffling+XOR operation, they behave in a manner similar to linear feedback shift registers (LFSR, http://en.wikipedia.org/wiki/Linear_feedback_shift_register) that are proven to produce uniform distribution in an optimal case.

In another embodiment of the invention the denoting values may be obtained by introducing the average of the estimated intermediate values into a pseudo-random number generator and the value output by the generator becomes the denoting value corresponding to the given intermediate value.

In an embodiment of the invention a structural rearrangement is performed in operational step S440 shown in FIG. 4. The structural rearrangement constitutes a trade-off between the width and the depth of the directed graph, manifesting itself in a trade-off between memory usage and arithmetic quantity. Conventional compilers apply structural rearrangement for small-sized graphs and partial graphs, because its complexity is at least $O(n*n)$. In an embodiment of the method according to the invention, the structural rearrangement is executed for the whole graph, as it is allowed by the complexity ($O(n*\log(n))$) of the algorithm applied for determining the denoting values.

In the embodiment of the inventive method shown in FIG. 4, a contraction is also performed as follows. The contraction is executed in operational steps S445 and S450 (see FIG. 4, bottom). In an embodiment of the method according to the invention, after the denoting values have been determined, the denoting values are recomputed corresponding to the edges of the directed graph obtained by the contraction, and the traversal sequence is also modified according to the contraction operation.

Operational step S440 is thereby followed by operational step S445, wherein the contraction is executed and the contraction coefficients are substituted in a manner described as follows. At the beginning of the method according to the invention the integral is initially computed as a non-contracted integral, and is transformed into a summation accordingly up to the point when contraction is computed. This means that up to that point computation is being performed as if the basis functions were primitive Gaussian functions.

Contraction, on the other hand, applies linear combinations of elementary Gaussian functions instead of the elementary functions themselves. The order of integration and linear combination can be swapped, and thus the contracted integral can be expressed utilizing the integrals of non-contracted Gaussian functions. Contraction may be computed utilizing for instance the PRISM algorithm presented in Gill's review. During contraction, the computation of a single integral is decomposed into computing several non-contracted Gaussian integrals (integrals of Gaussian functions). A number of these Gaussian integrals may be computed in the same way, and therefore in a well-optimized case such integrals have to be computed only once. The specific integrals that may be thus combined can be found utilizing known integral expansion rules. While performing contraction in the course of the method according to the invention, only those graph parts of the directed graph are multiplied which are not invariant to contraction. "Multiplying" graphs parts consists in substituting a graph part connected to a given node with multiple graph parts that are identical to the original except for their parameter values, and are connected to the given node with an addition operator. In an embodiment of the method according to the invention the contraction coefficients (the above specified Gaussian exponents: $\alpha$, $\beta$, $\gamma$, $\delta$, and the weights of the linear combination: $ca_i$, $cb_j$, $cc_k$, $cd_l$) are substituted into the integral in the operational step S445, when the contraction is executed on the graph.

By substituting the contraction coefficients into the graph, the coefficients do not have to be computed parametrically during the mapping of the integral. Thereby, the complexity of computation decreases, while at the same time the number of functions to be computed increases.

The constant propagation operation executed in operational step S450 is required by the substitution, in order to optimize out (execute) the operations that can be executed utilizing the constants (that is, those operations that are no longer parametric knowing the contraction coefficients). This yields a directed graph that has a significantly simplified structure.

After this step, the previously calculated denoting values are not usable any more, and therefore the denoting values have to be recomputed, i.e. the operational step S400 has to be repeated to obtain the denoting values also for the simplified-structure directed graph.

Figure 5:
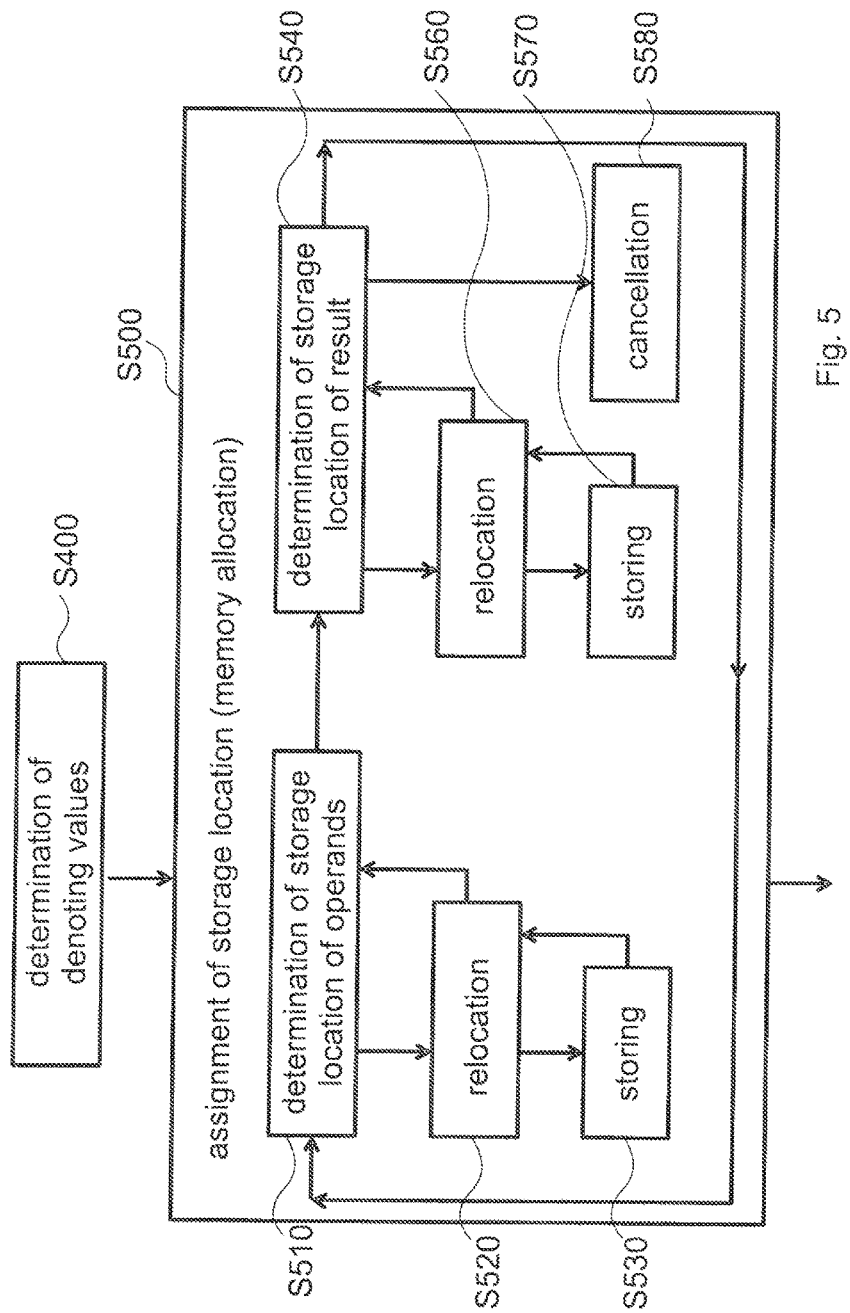
FIG. 5 shows a further part of an embodiment of the method according to the invention.

The above discussed steps are summarized in FIG. 5 that illustrates the manner of assigning storage locations during memory allocation, i.e. shows an operational step S500 of assigning storage locations. Operational step S500 is preferably executed after the denoting values have been obtained also for the simplified-structure directed graph in operational step S400. As shown in FIG. 5, first the storage locations of the operands are determined in operational step S510, that is, the operands of the operations corresponding to individual levels of the traversal sequence are found. In case an operand is found at more than one locations, that location is selected which can be accessed faster. At the same time, the program code for fetching the operand is also generated. In case there is no free space in the register storage, a relocation operation is performed in operational step S520, expediently by calling a corresponding relocation module. The relocation module removes an assignment of storage location of a low-priority value (which will be utilized only much later or not to be utilized again) from the storage on which the relocation operation is applied, and, in case it is needed later, the storage location of the given value is relocated in operational step S530 into a storage located lower in the hierarchy by means of calling a storage module. In case there is free space in a given storage, the storage location of the given value is assigned there. This is illustrated by the arrows connecting operational steps S510, S520, and S530. The modules also generate program code for the illustrated memory operations. After fetching the operands, in operational step S540 the storage location of the result of the operation is determined. First, it has to be decided whether the computation needs to be performed or it has been performed earlier (with the storage location of the result having been assigned somewhere in the memory). In operational step S570 the module executing the result storage operation also decides in which storage the storage location of the result should be assigned in an optimal manner. Before performing the storage operation, in operational step S560 certain selections have to be relocated. In case a given operation does not have to be performed, the corresponding steps are cancelled in operational step S580, specifying also the location of the result computed earlier. Next, the method is continued with the operation located on the next level of the traversal sequence that is illustrated by the arrow connecting operational steps S540 and S510.

As it has been mentioned above, certain parts of the directed graph may be identical in their graph structure, and thereby the results corresponding to these graph parts are not worth computing more than once. Accordingly, in an embodiment of the method equivalent graph parts are determined, the operations in the traversal sequence that belong to these equivalent graph parts are associated, and the operations belonging to the later occurrence of the equivalent part are removed from the traversal sequence, taking note of those graph part operations in the traversal sequence that belong to the later occurrence of the equivalent part. This operation has an effect similar to changing the structure of the directed graph belonging to the summation, that is, transforming the graph into a DAG (Directed Acyclic Graph) which may comprise cycles but does not comprise any directed cycles.

It has to be emphasized here that the graph is not really transformed—only note is taken in the traversal sequence of those graph parts that may be made to correspond to one another. A cycle may for instance form in this virtually transformed graph in case two computations make use of the same input coefficients, and the two results are then added up. Since in this case both directions point towards the end result, the resulting cycle is not a directed one. The above described substitution operation, however, should be used carefully, as it may increase the required number of registers. Therefore it is only performed in case the equivalent part of the graph has big enough size.

The invention also relates to a system for mapping an integral into a thread of a parallel architecture. The system according to the invention comprises an integral mapping module adapted for mapping the integral into a summation expressed by coefficient values and summation values, and a graph generation module adapted for generating a directed graph corresponding to the computation of the summation. In addition to showing the steps of the method according to the invention, FIG. 1 also illustrates the modules of the system according to the invention, which, following the conventional tripartite structure of compilers, are denoted by the expressions "Front-end", "Middle-end", and "Back-end" shown in the boxes corresponding to specific operational steps. Accordingly, FIG. 1 may also be interpreted such that the Front-end comprises the integral mapping module and the graph generation module. As shown in the figure, an integral is fed to the input of the Front-end, while its output is constituted by a directed graph that corresponds to the summation corresponding to the integral. The directed graph generated by the graph generation module is equivalent to the directed graph generated during the method according to the invention.

The system according to the invention further comprises a traversal sequence generation module adapted for assigning a level of a traversal sequence to each of the nodes, respectively. As shown in FIG. 1, the traversal sequence generation module, adapted to determine the traversal sequence, performs the functions of Middle-end. The input of the Middle-end is the directed graph generated by the Front-end, while at its output an architecture-independent program code is obtained. This code is essentially the "serialized" version of the directed graph, specifying the order of execution of the operations corresponding to the intermediate nodes.

The system according to the invention further comprises a memory allocation module adapted for specifying, at each level of the traversal sequence, a storage location of the intermediate value corresponding to the edge connected with its input to the node corresponding to the given level in a memory corresponding to the thread and comprising a register storage 10, a local storage 20, and a global storage 30. Essentially, the memory allocation module constitutes the Back-end, with the input thereof being the architecture-independent program code generated by the Middle-end, and the output being machine code, in which the entire memory allocation is defined. Thereby, the machine code has features specific to the given parallel architecture.

In the system according to the invention the above discussed heuristics can be applied for memory allocation (that is, for assigning the storage location of the intermediate values). Consequently, it may become necessary also in the system according to the invention to determine the intermediate level parameters, for which operation denoting values may be utilized.

Accordingly, in some embodiments the system according to the invention comprises an intermediate level parameter assignment module that comprises a random value generation module adapted for sequentially feeding at least one respective random value to the input nodes, an estimation module adapted for sequentially obtaining at least one respective estimated intermediate value at edges connected with their inputs to the intermediate nodes, and a denoting value assignment module adapted for assigning a respective denoting value to each edge based on the at least one estimated intermediate value. The intermediate level parameter assignment module is adapted for generating a denoting value table comprising the denoting values and the levels corresponding thereto, and for assigning the intermediate level parameters to the intermediate values based on the denoting value table.

In the above discussed embodiments of the invention, namely, where the intermediate level parameters are applied, multiple, preferably 20-110, particularly 30-40 respective random values are sequentially fed to the input nodes by the random value generation module. In these embodiments the multiple random values are selected preferably in a uniform manner from a characteristic range of input values.

In some embodiments of the system according to the invention optimization is performed on the directed graph assigned to the summation, and, accordingly, at least one equivalent transformation is performed on the directed graph utilizing a transformation module.

The invention is, of course, not limited to the preferred embodiments described in details above, but further variants, modifications and developments are possible within the scope of protection determined by the claims.

The invention claimed is:

1. A method of mapping an integral into a computational thread of a processing unit having a parallel architecture, the method comprising:
    mapping the integral into a summation of products, each of the products being a product of a respective coefficient value and a respective summation value;
    generating data elements that define a directed graph in a memory structure for computing the summation of products, the directed graph comprising:
        a plurality of input nodes, each corresponding to one of the coefficient values or to one of the summation values, being connected to an input of a first edge, and being adapted for giving the respective coefficient or summation value, as an intermediate value, to the input of the first edge connected thereto,
        one or more intermediate nodes, each corresponding to an operation of the summation of products and being connected to outputs of two of the first edges and to an input of a second edge, each intermediate node being adapted for performing the operation on the intermediate values of the two of the first edges, and for giving a result of the operation as another intermediate value to the input of the second edge connected thereto, and
        an output node being connected to an output of a second edge, and being adapted for receiving the intermediate value of the second edge;
    assigning a level of a traversal sequence to each node of the directed graph that defines a sequence in which operations corresponding to the nodes are executed in the computational thread of the processing unit; and
    specifying, for each level of the traversal sequence as the traversal is being performed according to the traversal sequence, a storage location in the memory structure for the intermediate value corresponding to each first or second edge having its input connected to the node assigned to the respective level of the traversal sequence, the specifying including determining a fastest memory location in a memory that includes register, local, and global storage locations by:
        storing the intermediate value in the register storage if:
            the register storage has free storage space, or
            there is another intermediate value that has been assigned a storage location in the register storage that has an intermediate level parameter with a value that is larger than the value of the intermediate level parameter of the intermediate value currently being assigned the storage location, in which case the storage location of the intermediate value with the highest intermediate parameter value is changed to the local storage or the global storage, otherwise
        storing the intermediate value in the local storage if:
            the local storage has free storage space, or
            if there is another intermediate value that has been assigned a storage location in the local storage that has an intermediate level parameter with a value that is larger than the value of the intermediate level parameter of the intermediate value currently being assigned the storage location, in which case the storage location of the intermediate value with the highest intermediate parameter value is changed to the global storage, otherwise
        storing the intermediate value in the in the global storage,
    wherein the arrangement and levels of the nodes defined by the memory structure maps the integral into the computational thread of the processing unit.

2. The method according to claim 1 further comprising:
after the levels of the traversal sequence have been assigned to each node of the directed graph, for each intermediate value:
    determining the level at which the intermediate value is utilized as the input of the operation corresponding to the intermediate node connected to the output of the first or second edge from which the respective intermediate value is received,
    determining a number of levels between the level at which the intermediate value is given to the input of the first or second edge and the level at which the intermediate value is utilized, and
    assigning the intermediate level parameter to the intermediate value, the intermediate level parameter having a value equal to the determined number of levels.

3. The method according to claim 2, wherein:
at least one respective random value is sequentially fed to the input nodes;
at least one respective estimated intermediate value is sequentially obtained at edges connected with their inputs to the intermediate nodes;
a respective denoting value is assigned to each edge based on the at least one estimated intermediate value; and
the intermediate level parameters are assigned to the intermediate values based on a denoting value table comprising the denoting values and the levels corresponding thereto.

4. The method according to claim 3, wherein between 30 and 40 respective random values are sequentially fed to the input nodes.

5. The method according to claim 4, wherein the multiple random values are selected uniformly from a characteristic range of input values.

6. The method according to claim 3, further comprising:
establishing the denoting values corresponding to the individual edges by:
generating shuffled values by shuffling the bits of the estimated intermediate values according to a predetermined sequence of operations, and
determining the denoting values by sequentially applying XOR logical operations to the shuffled values and contracting the shuffled values by the XOR logical operations.

7. The method according to claim 3, further comprising:
obtaining the denoting value at the output of a pseudo-random number generator into which an average of the estimated intermediate values is fed.

8. The method according to claim 3, further comprising:
performing, based on the denoting values, a contraction operation on the directed graph after the denoting values have been obtained;
recomputing the denoting values corresponding to the edges of the directed graph obtained by the contraction operation; and
modifying the traversal sequence according to the contraction operation.

9. The method according to claim 1 further comprising:
prior to assigning storage locations to the intermediate values belonging to each level of the traversal sequence, assigning two locations in the register storage for values of edges connected with their outputs to the node corresponding to the operation assigned to the given level of the traversal sequence.

10. The method according to claim 1, further comprising:
after generating the directed graph, performing at least one equivalent transformation on the directed graph.

11. The method according to claim 1, further comprising:
obtaining a hierarchical order of the summation values of the summation by iteration by:
numerically initializing a lowest order of summation values,
investigating a computational stability of higher orders of the hierarchical order of the summation values, and computing the higher orders based on the lowest order, and
applying forward iteration in case of the computational stability, or
applying iteration based on Chebyshev-approximation in case of a computational instability.

12. The method according to claim 1, further comprising:
specifying equivalent graph parts;
determining which operations in the traversal sequence belong to the equivalent graph parts;
associating each operation in the traversal sequence that belongs to an equivalent graph part with their respective graph part;
removing the operations belonging to the later occurrence of the equivalent part from the traversal sequence; and
identifying those graph part operations in the traversal sequence that belong to the later occurrence of the equivalent part.

13. The method according to claim 1, wherein the summation comprises contraction coefficients, and further comprising:

computing the contraction coefficients prior to the mapping;
storing the contraction coefficients in the memory; and
in the course of the method, fetching the contraction coefficients from memory.

14. A system for mapping an integral into a computational thread of a parallel architecture, the system comprising:
a processing unit having the parallel architecture; and
a memory including program code configured to, when executed by the processing unit, cause the system to:
map the integral into a summation of products, each of the products being a product of a respective coefficient value and a respective summation value;
generate data elements that define a directed graph in a memory structure for computing the summation of products, the directed graph comprising:
a plurality of input nodes, each corresponding to one of the coefficient values or to one of the summation values, being connected to an input of a first edge, and being adapted for giving the respective coefficient or summation value, as an intermediate value, to the input of the first edge connected thereto,
one or more intermediate nodes, each corresponding to an operation of the summation of products and being connected to outputs of two of the first edges and to an input of a second edge, each intermediate node being adapted for performing the operation on the intermediate values of the two of the first edges, and for giving a result of the operation as another intermediate value to the input of the second edge connected thereto, and
an output node being connected to an output of a second edge, and being adapted for receiving the intermediate value of the second edge;
assign a level of a traversal sequence to each node of the directed graph that defines a sequence in which operations corresponding to the nodes are executed in the computational thread of the processing unit; and
specify, for each level of the traversal sequence as the traversal is being performed according to the traversal sequence, a storage location in the memory structure for the intermediate value corresponding to each first or second edge having its input connected to the node assigned to the respective level of the traversal sequence, the specifying including determining a fastest memory location in a memory that includes register, local, and global storage locations by:
storing the intermediate value in the register storage if:
the register storage has free storage space, or
there is another intermediate value that has been assigned a storage location in the register storage that has an intermediate level parameter with a value that is larger than the value of the intermediate level parameter of the intermediate value currently being assigned the storage location, in which case the storage location of the intermediate value with the highest intermediate parameter value is changed to the local storage or the global storage, otherwise
storing the intermediate value in the local storage if:
the local storage has free storage space, or
if there is another intermediate value that has been assigned a storage location in the local storage that has an intermediate level parameter with a value that is larger than the value of the intermediate level parameter of the intermediate value currently being assigned the storage location, in which case the storage location of the intermediate value with the highest intermediate parameter value is changed to the global storage, otherwise storing the intermediate value in the in the global storage, wherein the arrangement and levels of the nodes defined by the memory structure maps the integral into the computational thread of the processing unit.

15. The system according to claim 14, wherein the program code is further configured to cause the system to:

sequentially feed at least one respective random value to the input nodes;

sequentially obtain at least one respective estimated intermediate value at edges connected with their inputs to the intermediate node;

assign a respective denoting value to each edge based on the at least one estimated intermediate value;

generate a denoting value table comprising the denoting values and the levels corresponding thereto; and assign the intermediate level parameters to the intermediate values based on the denoting value table.

16. The system according to claim 15, wherein between 30 and 40 respective random values are sequentially fed to the input nodes.

17. The system according to claim 16, wherein the multiple random values are selected in a uniform manner from a characteristic range of input values.

18. The system according to claim 14, wherein the program code is further configured to cause the system to:

perform at least one equivalent transformation on the directed graph.

19. The system according to claim 14, wherein the program code is further configured to cause the system to:

after the levels of the traversal sequence have been assigned to each node of the directed graph, for each intermediate value:

determine the level at which the intermediate value is utilized as the input of the operation corresponding to the intermediate node connected to the output of the first or second edge from which the respective intermediate value is received, determine a number of levels between the level at which the intermediate value is given to the input of the first or second edge and the level at which the intermediate value is utilized, and assign the intermediate level parameter to the intermediate value, the intermediate level parameter having a value equal to the determined number of levels.

* * * * *